US012667242B2

(12) United States Patent
Lebiedzinski et al.

(10) Patent No.: US 12,667,242 B2
(45) Date of Patent: Jun. 30, 2026

(54) INSERTION DEVICE

(71) Applicant: TJLE SPOLKA Z OGRANICZONA ODPOWIEDZIALNOSCIA, Olsztyn (PL)

(72) Inventors: Lukasz Lebiedzinski, Olsztyn (PL); Pawel Sadlo, Cracow (PL); Michal Brzezanski, Cracow (PL); Marek Szczypczyk, Cracow (PL); Michal Pyteraf, Cracow (PL); Damian Dziedzic, Cracow (PL); Konrad Sierotowicz, Cracow (PL); Jakub Szczerbuk, Olsztyn (PL); Tien-Ho Huang, Olsztyn (PL); Kamil Sumera, Cracow (PL); Grzegorz Biernacki, Brzezie (PL)

(73) Assignee: TJLE SPOLKA Z OGRANICZONA ODPOWIEDZIALNOSCIA, Olsztyn (PL)

( * ) Notice: Subject to any disclaimer, the term of this patent is extended or adjusted under 35 U.S.C. 154(b) by 273 days.

(21) Appl. No.: 18/558,565

(22) PCT Filed: Feb. 9, 2022

(86) PCT No.: PCT/EP2022/053182
§ 371 (c)(1),
(2) Date: Nov. 2, 2023

(87) PCT Pub. No.: WO2023/020717
PCT Pub. Date: Feb. 23, 2023

(65) Prior Publication Data
US 2024/0215805 A1 Jul. 4, 2024

(30) Foreign Application Priority Data

Aug. 20, 2021 (EP) .................................... 21461577

(51) Int. Cl.
| | |
|---|---|
| *A61B 1/005* | (2006.01) |
| *A61B 1/00* | (2006.01) |
| *A61B 1/05* | (2006.01) |

(52) U.S. Cl.
CPC ...... *A61B 1/00105* (2013.01); *A61B 1/00042* (2022.02); *A61B 1/00126* (2013.01); (Continued)

(58) Field of Classification Search
CPC .............. A61B 1/00105; A61B 1/0057; A61B 1/00042; A61B 1/00052; A61B 1/00126; (Continued)

(56) References Cited

U.S. PATENT DOCUMENTS

| | | | | |
|---|---|---|---|---|
| 2007/0093755 A1* | 4/2007 | Koos | ................... | A61M 1/7415 604/35 |
| 2014/0066716 A1* | 3/2014 | Arai | ..................... | A61B 1/0057 600/149 |

(Continued)

FOREIGN PATENT DOCUMENTS

| | | |
|---|---|---|
| JP | 2016054967 A | 4/2016 |
| PL | 220015 B1 | 8/2015 |

(Continued)

*Primary Examiner* — Michael J Carey
*Assistant Examiner* — Olivia Grace Starkey
(74) *Attorney, Agent, or Firm* — FisherBroyles, LLP; Ronni S. Jillions

(57) ABSTRACT

An insertion device including a handle, a flexible shaft elongated at least in part with a movable distal portion controllable by a user interface, and a driving system for transforming actuation from the user interface to movement of the distal portion. The driving system has a housing leak-tightly connected to the shaft from one side and from the opposite side the housing is provided with the first detachable leak-tight fastener, whereas the handle is provided with the second detachable leak-tight fastener. A method of preparation for reuse of an insertion device in (Continued)

which the shaft is subjected to the treatment of at least one agent wherein subjected to disinfection is shaft with the driving system, whereas the handle with the user interface is detached from the driving system for the disinfection time.

8 Claims, 7 Drawing Sheets

(52) U.S. Cl.
CPC ........ *A61B 1/00128* (2013.01); *A61B 1/0052* (2013.01); *A61B 1/0057* (2013.01); *A61B 1/00052* (2013.01); *A61B 1/05* (2013.01)

(58) Field of Classification Search
CPC ..... A61B 1/00128; A61B 1/05; A61B 1/0052; A61B 2017/0046
See application file for complete search history.

(56) References Cited

U.S. PATENT DOCUMENTS

| | | | |
|---|---|---|---|
| 2014/0107416 | A1 | 4/2014 | Birnkrant |
| 2015/0112143 | A1* | 4/2015 | Ando .................... A61B 1/0052 |
| | | | 600/149 |
| 2020/0221932 | A1 | 7/2020 | Ouyang et al. |
| 2021/0338052 | A1* | 11/2021 | Ouyang ............. A61B 1/00128 |
| 2022/0079418 | A1* | 3/2022 | Ouyang ............... A61B 1/0016 |
| 2022/0265967 | A1* | 8/2022 | Alhadeff ........... A61M 25/0136 |
| 2022/0304549 | A1* | 9/2022 | Iijima ................ A61B 1/00105 |

FOREIGN PATENT DOCUMENTS

| | | |
|---|---|---|
| WO | 2007080989 A2 | 7/2007 |
| WO | 2013150871 A1 | 10/2013 |
| WO | 2017040692 A1 | 3/2017 |

* cited by examiner

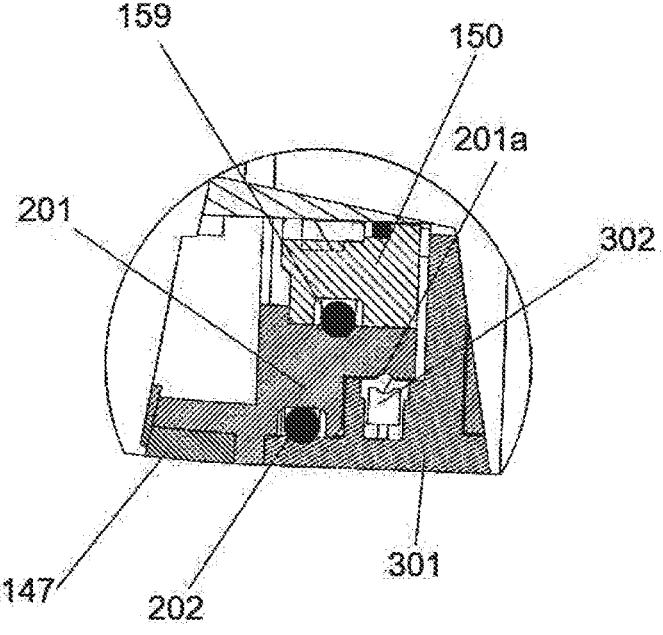
Fig. 1b
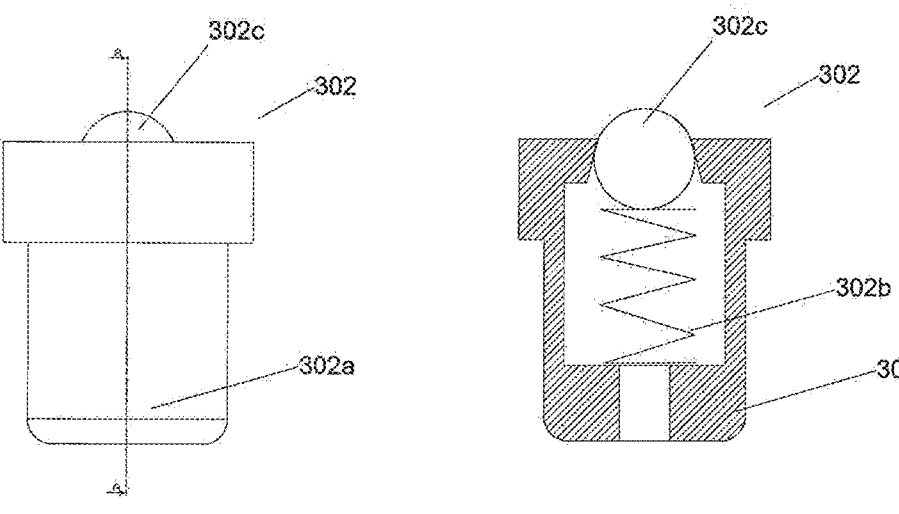
Fig. 1c                              Fig. 1d

INSERTION DEVICE

TECHNICAL FIELD

The subject of the invention is an insertion device and a method of preparation of the insertion device for reuse, in particular an endoscope.

BACKGROUND ART

Insertion devices, such as endoscopes, find application in numerous fields, in particular in medicine. The endoscope is constructed of a handle and a working end, so called an indenter, ended with a distal portion, in particular movable distal portion. The endoscope can be also used as a part of an endoscopic system. Means enabling procedures and examination, most often means enabling the transfer of image or acquisition of parameters from other sensors, are located in the distal portion. The indenter can be also provided with means for providing medicines or other substances or even surgical tools. The combination of afore-mentioned means can also be used. The use of the movable distal end, controlled by means of a user interface, the most often a mechanical interface, in particular by a lever located on the handle enables the optimal placement of the distal portion with regard to an operating field and carrying out the examination by endoscope in more accurate and less inva-sive way. The movable distal portion is engaged with the user interface. The endoscope additionally comprises a camera on the end or a lens and means for transferring the image along the shaft.

Typically, the movable distal portion is steered by means of at least one cable member. By using two (or more) cable members, an additional control of twisting of the movable distal portion can be obtained. Also other numerous tech-niques of steering the movable distal portion of the endo-scope are known, including pneumatic, hydraulic and other.

In endoscopes various gears are used, transmitting the movements of the operator interacting with the mechanical interface to the movements of the distal portion of the shaft. For example, in the document JP2016054967, the endo-scope with connection rod gear in which force is transmitted by a pusher 24 is disclosed.

In document WO2013150871, an endoscope with a con-nection rod gear is also disclosed. Additionally, a need to provide leak-tightness of a shaft and a movable distal portion is identified. The connection rod gear was used also in the solution according to the document WO2007080989, in which an endoscope with additional functions requiring exceptional leak-tightness was discussed as well as a need of use of materials resistant to disinfection agents for construc-tion of controlling system of the endoscope was raised, in order to decrease degradation in the course of disinfection and sterilization.

In the state-of-the-art also other mechanisms of the gears for medical use are known. From the Polish patent Pat. 220015 a surgical tool is known, provided with a guide with a controlling pusher, wherein an end of the guide, on which a surgical instrument is seated, is connected to a substantial portion of the guide by means of an articulation. The end of the controlling pusher is connected through an eccentric intermediate element to an executive pusher, which is dedi-cated to transmission of the drive to the surgical instrument. The eccentric intermediate element is rotatably seated in a bending axis of the articulation, and the controlling pusher and the executive pusher are connected rotatably with the eccentric intermediate element. In a substantial part of the guide, a bending pusher runs through, which end is fixed rotatably to the guide end. The eccentric intermediate ele-ment can have a form of two-armed connector, whose arms are advantageously at an angle to each other equal to 135°, or alternatively it can be in the form of a disc.

Document WO2017040692 discloses an endoscope and related method that comprise a proximal handle and a distal shaft having an movable insertion end. It has a drive for applying force moving the movable insertion end. The shaft is detachable from the handle.

The flexible endoscopes known in the state-of-the-art are prone to mechanical damages, in particular their shafts, movable end portions and cable members. Due to the fact that endoscopes have contact with a patient, they have to be prepared to reuse after each procedure, cleaned, disinfected and/or sterilized, what additionally contributes to frequent mechanical and chemical damages of the whole device. The need to secure the handle with the user interface—and in endoscopes with a screen also the screen—makes the pro-cess of disinfection troublesome and not insufficient protec-tion contributes to the fast wearing of those elements.

Problem to be Solved

Solutions known in the state-of-the-art do not provide the possibility of multiple use of the insertion device in a safe way for the patient, without exposing elements sensitive to damages during exposition on aggressive methods and cleaning, disinfecting or sterilizing agents.

SUMMARY OF THE INVENTION

The objective of the invention is to solve aforementioned problems.

An insertion device according to the invention comprises of a handle, an elongated shaft at least partly flexible, having a movable distal portion controllable by means of a user interface and a driving system for transforming actuation from the user interface to movement of the movable distal portion. At least one cable member is connected to the movable distal portion from one side, extending along the shaft and connected to the driving system from the opposite side, whereas the driving system is suitable for converting of the actuation from the user interface to a translatory motion of the cable member. The driving system has a housing leak-tightly connected to a shaft from one side and from the opposite side the housing is provided with first detachable leak-tightly fastening means. The handle is provided with second detachable leak-tight fastening means suitable for being leak-tightly connected to the first fastening means directly or by the means of an additional element. Moving the drive to the shaft through a sealed connection of the shaft with the driving system provides a possibility to detach the insertion device during a disinfection time and to separate the sensitive handle from the erosive process of disinfection. The driving system is suitable for receiving an actuation signal from the user interface via leak-tight connection of the housing with the handle. Thanks to that sole the actuation signal is transmitted, the connection is easier to be detached. When the handle is to be disconnected from the elongated shaft the connection between the user's interface and the distal portion of the elongated shaft need to be interrupted. It is difficult to interrupt the cable that conveys pulling force to the distal portion and then to easily connect it again when handle and elongated shaft are re-attached. The invention may be used in different ways, and it works independently from the way a torsional force is indeed applied to the movable distal portion. Location of the driving system together with the shaft is crucial. Thanks to that configuration, the shaft with the driving system can be disconnected in such a manner that only actuation signal conveying means are interrupted and there is no need to break drive conveying means which is difficult and prone to malfunction. The cable which is conveying the drive to the distal portion is uninterrupted. That makes sealing the disconnected elongated shaft with the drive easier as well as makes it more convenient and faster to detach and re-attach. The invention enables cleaning, disinfection and/or sterilization of the shaft using different methods, makes sterilization of the shaft without sterilizing the handle possible, or even the use of single-use shafts easier.

Advantageously, housing of the driving system is closed with a leak-tight partition.

Advantageously, the driving system constitutes a pull-push gear with an eccentric intermediate element, to which from one side reciprocally two cable members are attached and from the opposite side the eccentric intermediate element is engaged reciprocally with a first piston and a second piston. In the leak-tight partition there are two openings, through which the first piston and the second piston pass so that the first piston and the second piston are sealed in the openings of the partition by the means of sealing means and they reciprocally affect the pull-push gear. The user interface can be a lever connected to a first pusher and a second pusher suitable for pushing the first piston and the second piston, respectively.

Advantageously, the movable distal portion is provided with an imaging device connected to a screen placed in the handle, by means of a connector of the housing provided in the housing of the driving system and a connector of the handle provided in the handle.

Advantageously, the connector of the housing or the connector of the comprises handle leak-tight electric connector as, e.g., touch connectors such as pogo-pins and/or an optical connector, which facilitate the fast transmission of the signals and/or illumination while maintaining the leak-tightness.

In the housing of the gear advantageously a light source is located.

Advantageously the first fastening means comprise a threaded connection with a gasket.

Advantageously the first fastening means and the second fastening means are complementary in fixed orientation—thanks to that they can be connected directly, and/or using further elements and it is easy to detach and reattach the device and keep it fully operational.

Advantageously the device is provided with an intermediate element suitable for connecting to the first and the second fastening means. Thanks to that a universal interface suitable for using of wider spectrum of handles and driving systems can be used.

Advantageously the housing of the driving system is provided with the pneumatic connector and/or optical connector.

A method according to the invention concerns a method of preparation for reuse of an insertion device provided with a handle, a flexible elongated shaft, at least in part with a movable distal portion, controllable by means of user interface by a cable member connected to the movable distal portion extending along the shaft towards the handle, and a driving system suitable for converting of the actuation from the user interface to the movement of the distal portion of the shaft, wherein the shaft is subjected to the treatment of at least one cleaning, disinfecting or sterilizing agent, chosen from the group comprising: chemical agents, agents acting physically/chemically as e.g. thermal agents, radiation, ultrasound waves, agents acting mechanically and agents acting physically or their combination. The sealed shaft with the driving system is subjected to cleaning, disinfection and/or sterilization separately, by detaching it from the handle before subjecting it to at least first cleaning, disinfecting or sterilizing agent. Thanks to that the handle needs not to be exposed to more aggressive agents required in shaft preparation.

During application of the said first agent, the driving system is sealed by means of a sealing cover for a time of disinfection. Such solution enables using the driving systems with a housing without the sealed partition. In solutions with sealed partition, the cover constitutes an additional protection reducing a risk of exposition of the mechanism for the erosive procedure of preparing for the reuse. The sealing cover is connectable easily as the housing of the driving system, and it is provided with leak tight fastening means.

Advantageously the handle is subjected to a treatment of the second cleaning, disinfecting or sterilizing agent, having lower concentration, of other composition, concentration, or which is applied over a different—typically shorter—period of time.

Advantageously the shaft is subjected to the leak-tightness test by means of a pneumatic connector provided in the part of the housing of the driving system.

DESCRIPTION OF FIGURES

The subject of the invention was presented with reference to its embodiments presented in attached drawing, wherein FIG. 1b presents this connection in magnification, FIGS. 1c and 1d present a snap-in element, in side view and cross-section respectively.

DESCRIPTION OF EMBODIMENTS

Figure 1A:
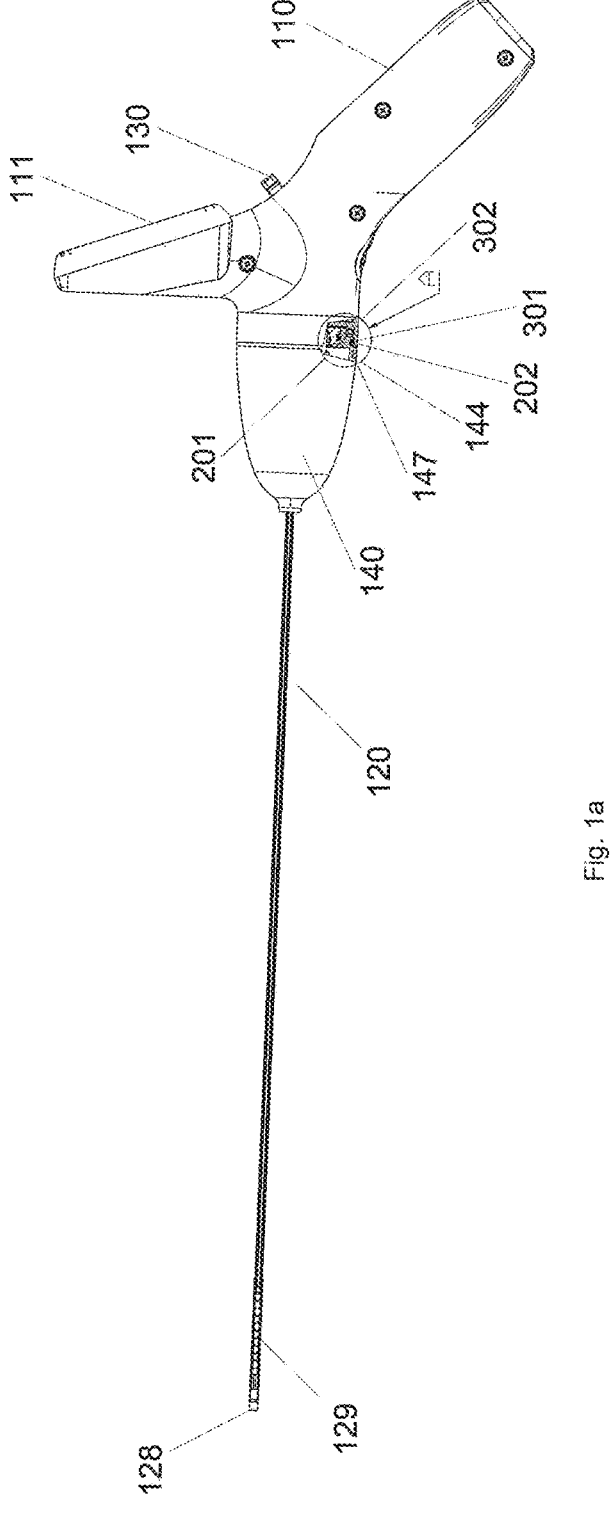
FIG. 1a presents an embodiment of the insertion device in side view, with a partial uncovering of the connection between the handle and the housing of the driving system.

The insertion device according to the embodiment of the invention presented in FIG. 1a constitutes an endoscope comprising a handle 110, on which a lever constituting a user interface 130 and a screen 111 are provided. A flexible shaft 120 with a movable distal portion 129 is connected to the handle 110 via the driving system, in this embodiment a mechanical more precisely a pull-push gear 140. Alternatively, the insertion devices stiffened on part of their length or semi-stiffened can be used. The driving system 140 is closed in the housing 144 with a shield 147.

Movable distal portion 129 of the shaft 120 is controllable by means of the user interface 130 via a cable member. Additional control is obtained by using more cable members. In general, one cable member is sufficient, and in the embodiment discussed below two cable members were used: a first cable member 121 and a second cable member 122 connected to the movable distal portion 129 running along the shaft 120 towards the handle 110.

The force which is moving the distal portion 129 is applied to two cable members 121, 122 by means of the driving system 140. Although in the present embodiment two cable members were used using an elastic distal portion, a simplified solution with one cable member can be proposed.

Using of two cable members and the mechanical gear as a driving system 140 complicates the problem of providing a modular device, in which the handle and the shaft are detachable. However, in such configuration, a reliable haptic feedback between a movement of the distal end and user interface 130 is obtained.

The driving system 140 has a housing 144 leak-tightly and permanently connected with the shaft 120. Connection between the housing 144 and the handle 110 is detachable. From the handle 110 side, the housing 144 is leak-tightly closed with the partition 150. Thanks to such configuration it is possible to detach the shaft from the handle and to disinfect it without additional procedures.

The housing 144 of the driving system is provided with the first detachable leak-tight fastening which constitute profiles 201 of the connector of the housing and the socket 201a and a gasket of the housing 202. The profiles 201 of the connector of the housing are placed in a way to provide space for the gasket 202, which is visible in FIG. 1a presented as detail A and shown in magnification in FIG. 1b.

The handle 110 is provided with the second detachable leak-tight fastening means, which constitute profiles 301 of the connector of the handle and snap-in elements 302. The second detachable leak-tight fastening means are suitable for being connected leak-tightly with the first leak-tight fastening means 201, 201a, 202.

In the embodiment illustrated in FIG. 1a and FIG. 1b, first leak-tight fastening means constitute profiles 201 of the connector of the housing 144 of the driving system 140 and socket 201a suitable for receiving an snap-in element 302 of the handle provided in the profile 301 of the connector of the handle 110. The profiles 301 of the connector of the handle and the snap-in elements 302 of the handle constitute the second fastening means. In present embodiment the profile 301 of the connector of the handle and profile 201 of the connector of the housing are complementary. The gasket 202 provided in the groove of the profile 201 of the housing at the connection of the first and the second fastening means is supported by the profile 301 of the connector of the profile, sealing the connection 144 of the driving system 140 with the handle 110.

Ball-plungers presented schematically in FIG. 1c in side view and in FIG. 1d used as snap-in elements 302 have that advantage, that they provide an easiness of attaching and detaching while simultaneous leak-tightness and stability is obtained by using gaskets visible in the cross-section. The ball-plunger comprises a body 302a with an opening. In the body 302a, the ball made of stainless steel 302c is located, having the diameter bigger than the diameter of the opening. The ball is pressed to the opening by springing means 302b. Thanks to such construction of the snap-in, the ball blocks the complementary fastening means in the form of socket 201a in the profile 201 without a clearance.

A leak-tight connection of the first and the second fastening means provides insensitivity of the device to dirt during the operation and the possibility of cleaning, disinfection and/or sterilization.

For cleaning, disinfection and/or sterilization of particular parts of the endoscope by means of aggressive agents, the sealed shaft 120 with the driving system 140 is detached from the handle 110 before subjecting it to the action of at least one cleaning, disinfecting or sterilizing agent and the handle 110 is subjected to the action of other, of other concentration, intensity, or other time of reaction cleaning, disinfecting or sterilizing agent. Thanks to that, particular parts can be disinfected and sterilized separately from each other, choosing various methods or their combination, depending on the purpose, risk and contamination of different parts of the device. The isolation of the driving system to the shaft and providing the detachability of the handle enables the selection of various ends, depending on the patient and the procedure, such as various lengths, diameters and additional functions as, e.g., working channel. It enables also repair or replacement of only worn out, or broken parts of the device. Disinfecting agents will not get inside the driving system and the shaft causing the corrosion of the mechanism and the cable members due to the leak-tightness of the partition 150. Additional protection can be obtained by using the cover attachable to the first and/or further leak-tight fastening means, provided with the fastening means complementary to the first fastening means. With such solution, the partition 150 need not be leak-tightly connected to the housing 144 of the driving system 140.

Detachable connection between the housing 144 of the driving system 140 and the handle 110 can be realized in a variety of ways. Both elements can form together a quick connector working on the same principle as connectors in pneumatic connectors known by the person skilled in the art. A thread and a gasket can be also used. Between the housing 144 of the driving system 140 and the handle an intermediate element suitable for being connected to the first and the second fastening means can be used. Such element can be a muff provided with the fastening means complementary with the first and the second fastening means, located between the handle 110 of the insertion device and the housing 144 of the driving system 140.

The driving system 140 is suitable for receiving an actuation signal from the user interface 130. Such actuation should be transmitted through the leak-tight connection of the housing 144 with the handle 110. In present embodiment, the actuation constitutes a mechanical pressure transmitted by deflecting the lever constituting the user interface 130 in a way illustrated in FIG. 2a and FIG. 2b.

The housing 144 is leak-tightly closed by the partition 150 provided with the openings 151, through which the first piston 141 and the second piston 142 are passed. Openings 151 are sealed around the openings with a seating means, e.g., o-rings 152—strictly each opening is sealed with a pair of o-rings. Alternatively, simmer rings can be used, x-rings or liquid sealing. Such solutions provide a leak-tight operation of the pistons 141, 142 in the openings 151. The connection of the shaft 120 with the housing 144 of the driving system 140 is sealed—seals 149 constitute two o-rings.

The force from the lever constituting the user interface is transmitted to the pistons by means of the pushers 131, 132 engaged with the lever by means of rotatably mounted swinging element 133.

The first cable member 121 and the second cable member 122 are connected to the movable distal end 129, the opposite ends of the cable members are connected to the eccentric element 143. As it is visible in FIG. 3*f*, the cable members 121, 122 were guided along the shaft in the cable housings 121*a*, 122*a*. Thanks to reciprocal operation of the pistons 141, 142, pushing the first piston 141 causes the retraction of the second piston 142 and such rotation of the eccentric element 143, that the second cable member 122 leak-tightens and the first cable member 121 loosens. Analogously, pushing the second piston 142 causes the retraction of the first piston 141 and such rotation of the eccentric element 143, that the first cable member 121 leak-tightens and the second cable member 122 loosens. Such systems tend to jam. This can be prevented in various ways, one of the simplest is to provide a tiny clearance—in the range of 0.1 to 1 mm between pushers and pistons, or by providing stoppers to limit travel of the eccentric element and/or the pushers.

Thanks to the configuration described above, by making a sterilization of the insertion device, the whole shaft 120 together with the driving system 140 and cable members 121, 122 can be separated from the handle 110 and disinfected by means of the aggressive agents and at the high temperatures. Such type of disinfection has a damaging effect on the handle, so as a result the lifetime of the insertion device is significantly elongated. Cable members 121, 122 are protected from the effect of the aggressive cleaning, disinfecting and/or sterilization means as they are enclosed inside sealed drive housing and elongated shaft.

The handle 110 is provided with its own electronic systems and a power and signal supply/exchange system. They are connected with the driving system by means of the group of wires 114 and the connector of the handle 113, complementary with the connector 153 of the housing provided in the partition 150—as shown in FIG. 2*b*. At the opposite side of the partition 150 a printed circuit 160 is located, to which the connector 153 of the housing fed the electric signals.

An important protection is the sealing of the housing 144 of the gear 140 from the side, of which it is attached to and detached from the handle 110. Due to that fact the housing 144 is provided with the leak-tight partition 150. At the opposite side of the partition 150, the circuit board 160 is connected to the connector 153 of the housing.

For the leak-tightness of the partition, the realization of the coupling between the gear 140 and mechanical user interface 130 is important. For effective performance of the endoscope, the mechanical user interface 130 must affect the gear 140, which transfers the impact on the cable members steering the movable distal end 129 of the shaft 120.

Figure 2A:
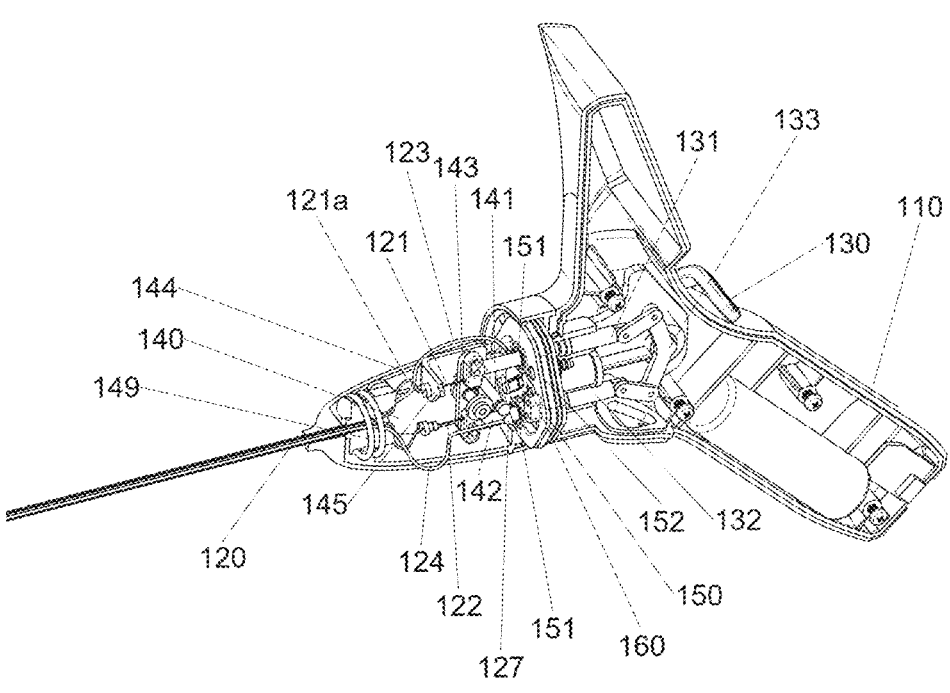
FIG. 2a presents the device in this embodiment in partial cross-section, in perspective view
Figure 2B:
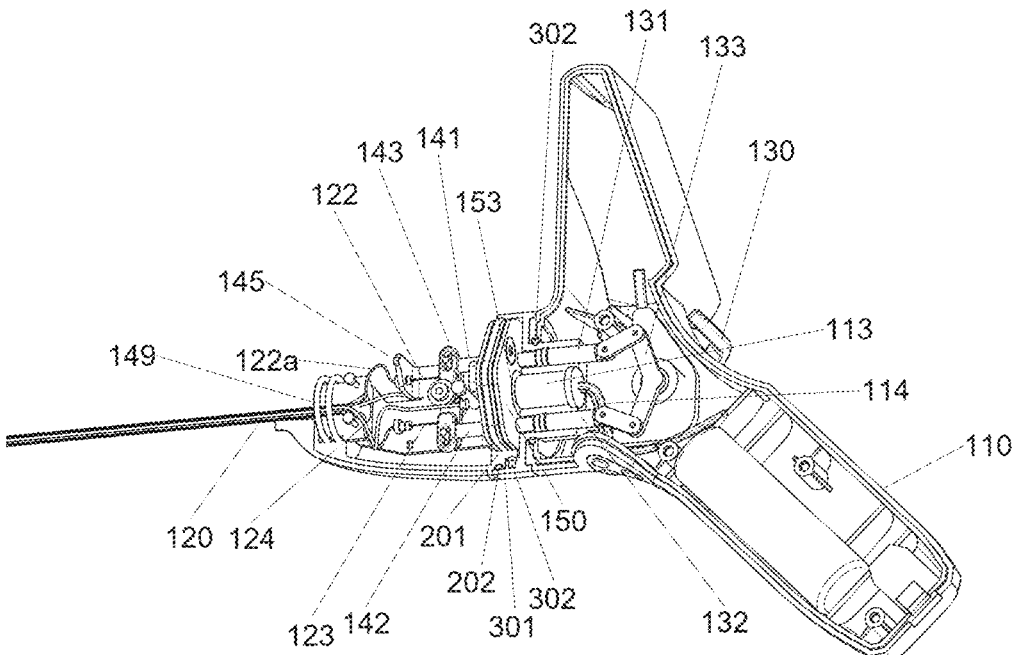
FIG. 2b presents the device in this embodiment of the invention in partial cross-section, in other perspective view.

In the embodiment presented in FIG. 2*a* and FIG. 2*b*, the partition 150 is partially thicker at the openings 151 and in its whole length of the openings 151 in the partition the cylinders were integrated, inside which sealing o-rings were located. One is enough, but two provides better reliability. It is also possible to use a greater number of sealing elements.

Greater reliability of sealing is obtained with two or greater number of o-rings, but the leak-tightness can be achieved with one o-ring in each opening. Alternatively, simmerrings can be used.

A non-exclusive alternative for the leak-tight partition 150 is using an additional cover for disinfection, connected to the first fastening means for the time of disinfection.

Leak-tightness between the shaft 120 and the housing 144 of the driving system 140 is provided by entering the shield 147 of the housing 144 on the shaft and by sealing the shaft by means of the sealing 149 of the shaft from the inside of the housing 144.

Figure 3A:
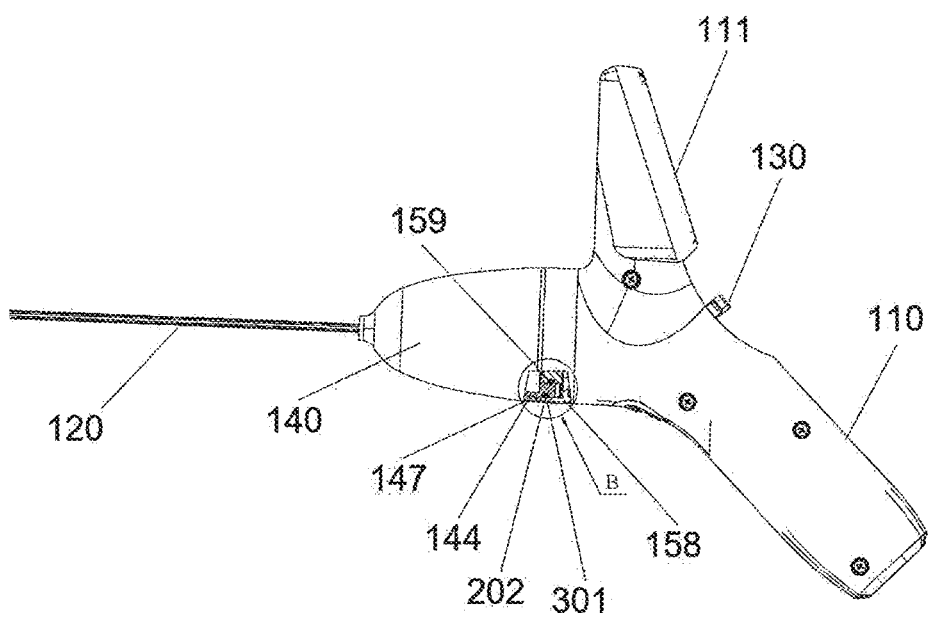
FIG. 3a presents this embodiment of the insertion device in the side view with partial uncovering of the connection between the housing of the driving system with a partition.
Figure 3B:
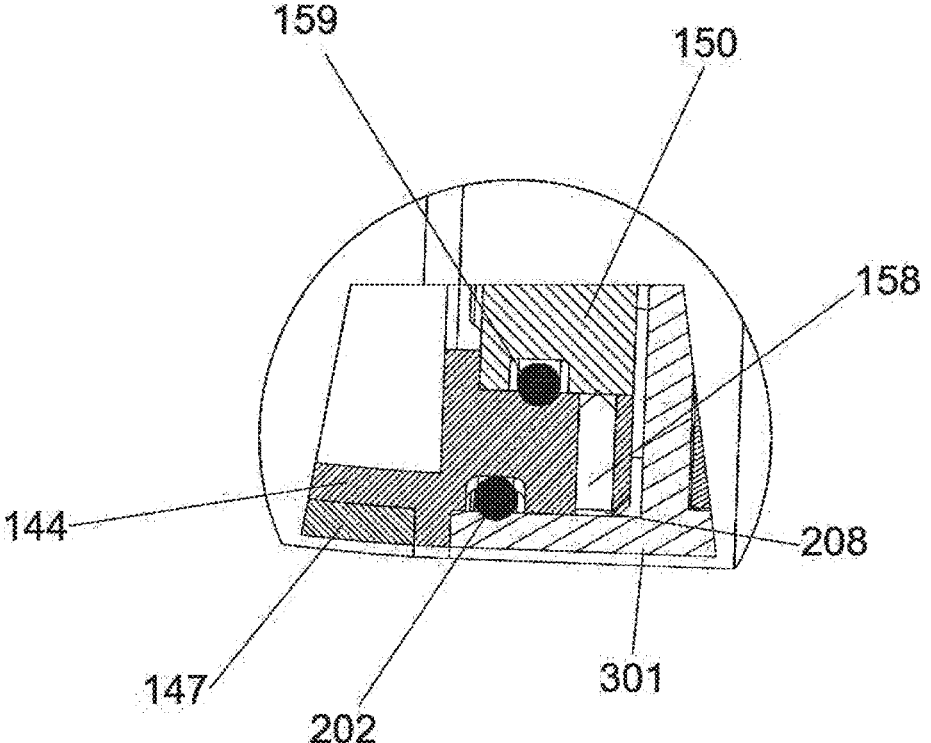
FIG. 3b presents this connection in magnification.
Figure 3C:
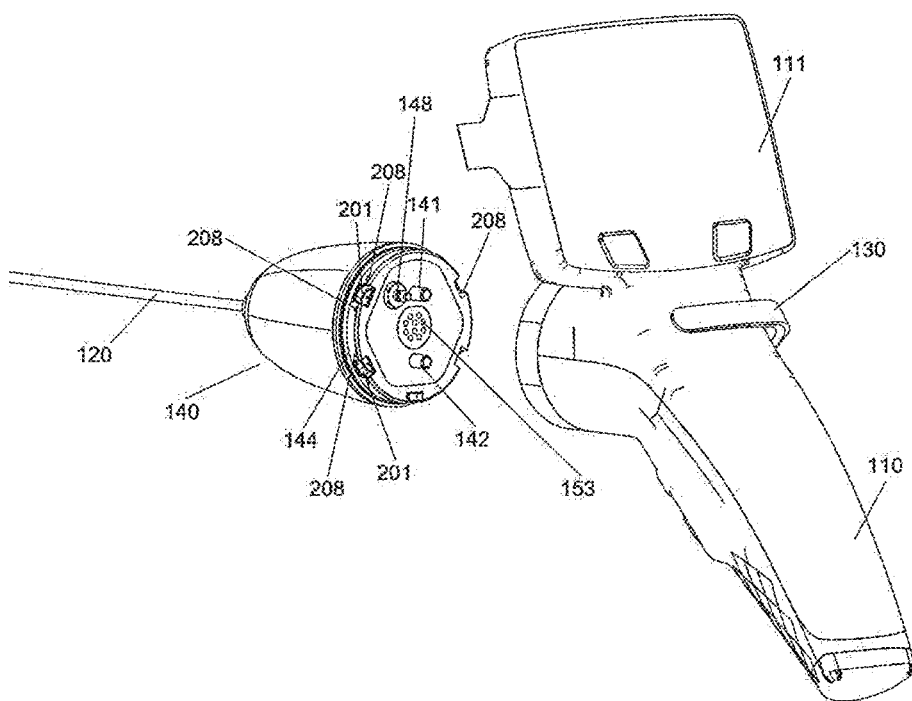
FIG. 3c presents the handle and the shaft detached from it with the driving system in the perspective view.
Figure 3D:
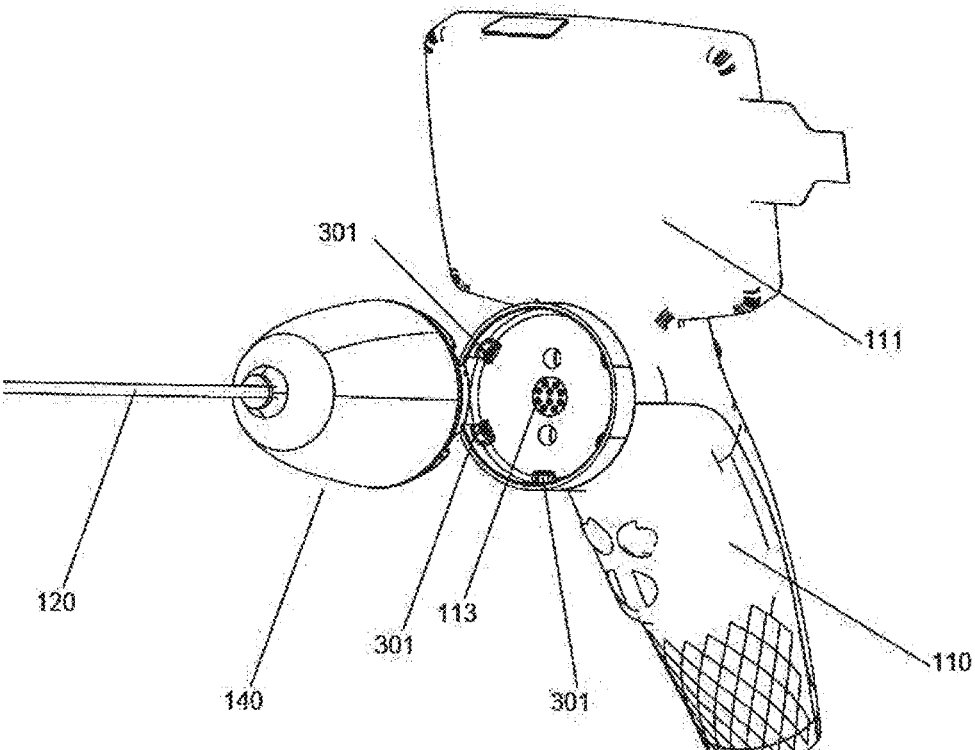
FIG. 3d presents the handle and the shaft detached from it with the driving system in the other perspective view, FIG. 3e present the housing of the driving system in the partial decomposition in the perspective view.

A method of connecting the partition 150 with the housing 144 was illustrated in FIG. 3*a*—detail B shown in magnification in FIG. 3*b*. The partition 150 is provided with the groove in which the gasket 159 is located, supported by the edge of the housing 144. In the edge of the housing 144 the openings 208 are provided, through which screws 158 connecting the partition 150 with the housing 144 are passed. The openings 208 are provided in the proximity of the profiles 201—as shown in FIG. 3*a*. As is shown in FIG. 3*c* and FIG. 3*d*, the distribution of the profiles 201 in the housing 144 and the profiles of the connector of the handle 301 corresponding to them were geometrically matched so that there will be only one possible orientation of the housing 144 in relation to the handle 110. In such way, the errors of users during the connection are eliminated and it facilitates the operation.

The movable distal portion 129 is provided with the imaging device 128 electrically and/or optically connected to the screen 111 located on the handle 110. This connection runs through the circuit board 160 and the detachable connector 153 of the housing provided in the leak-tight partition 150 and the connector of the handle 113 complementary with it. In the connector 153 of the housing pogo-pins matching the connector of the handle 113 performed well. It is also possible to use other type of the connectors—in particular leak-tight connectors. The contact of the connectors 153 and 113 for the work convenience should be easy to detach or only pressed on each other. The connector 153 of the housing serves to transmit the electric signals or other signals and if needed also power supply form the handle 110 to the driving system or other systems encompassed within the housing of the driving system or within the elongated shaft.

Figure 3E:
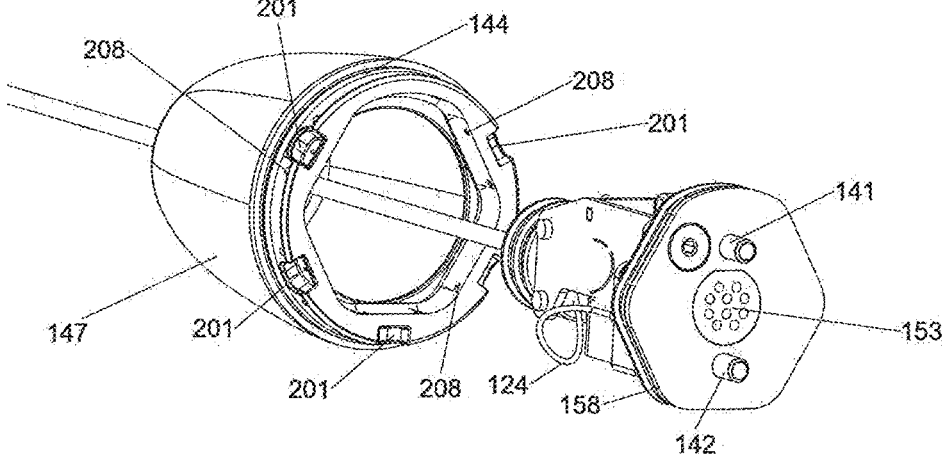
FIG. 3f presents the housing of the device and the shaft detached from it with the driving system in the partial cross-section, in perspective view.
Figure 3F:
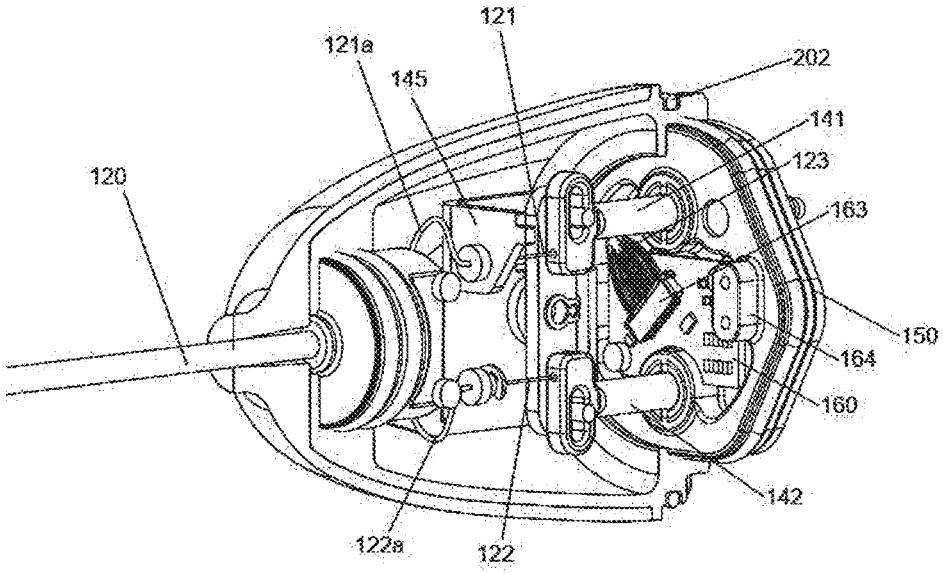

As it is visible in FIGS. 3*e* and 3*f*, the housing 144 of the gear 140 provides enough space to locate the circuit board 160 in it, transmitting and processing electric or other signals. For mounting the circuit board and the eccentric element in the housing 144, the carcass 145 was provided. Said circuit board 160 is connected to the connector 153 of the housing. Locating the light source 164 on the circuit board 160 enables easy transmission of light along the shaft 120. The light from the light source 164 is guided via the collector 127 to the optical fiber 124, which guides it to the movable distal portion 129. The imaging device 128 is connected to the circuit board 160 by means of the wire 123 and the connector 163 of the circuit board, to which the wire 123 is connected. The wire 123 serves for the image transmission from the imaging device 128 to the screen 111 and to connect the imaging device with an energy storage provided in the handle 110, or other power supply. The wire 123 may constitute multi-core wire and may serve for signal transmission to and from the additional sensors and tools provided in the shaft.

The shaft 120 may be lighted directly from the interior of the housing 140 or transmit the light by the optical fiber to the movable distal portion. Alternatively, the image guide may be used and an ocular may be provided on the handle 110 instead of the screen 111.

It is also admissible to abandon the leak-tight partition 150. Then, the leak-tightness depends only on the reliability of the fastening means 201, 202, 301, 302. The electrical connection between the handle 110 and the circuit board 160 may be provided with a common pin on the board. Then, for disinfection using an additional cover is necessary, connected leak-tightly with the first fastening means 201, 202.

In the described embodiments of the insertion device according to the invention, sub-assemblies in the working end are separated from the sub-assemblies in the handle. In this way only the working end (or the handle) must be sent for repairing or replacing in case of defect. It is the repairs and the downtimes connected with it, which constitute the main cost of flexible endoscopes use. Fast replacement of the working parts before the procedure enables for shortening the preparation time for the procedure and to increase the number of procedures. The driving system permanently connected to the shaft enables attaching and detaching the parts of the endoscope to and from each other by the user without the use of tools. The leak-tightness enables disinfection and sterilization to be independent of each other. The distribution of the profiles 201 and 301 is chosen so that by their connecting only one orientation is admissible—thanks to that the proper electric and/or optical signals transmission is provided.

Disinfection is carried out with the shaft 120 detached, which is subjected to the operation of at least one disinfection agent chosen from the group comprising chemical agents, thermal agents, radiation, ultrasound waves. The leak-tight shaft 120 with the driving system 140 is subjected separately to cleaning, disinfection and/or sterilization, by its detaching from the handle 110 before subjecting it to the operation of at least one cleaning, disinfecting, or sterilizing agent and the handle 110 is subjected to the operation of other cleaning, disinfecting or sterilizing agent with other concentration, intensity or time of reaction.

Additionally, optionally the shaft is subjected to the leak-test by means of the pneumatic connector 148 provided in the housing of the system 144. For carrying out such trial, it is enough to pump the shaft up to the predefined pressure value, and after the predefined time to perform the measurement of the pressure in the shaft 120, measuring it with the manometer by means of the connector 148. Such test decreases the risk of an unexpected break-down of the shaft. However, frequent leak-tests speed up wear of sealing means and translate into the shorter lifetime of the shaft. The pneumatic connector 148 should be protected from the dirt and from the operation of the cleaning and disinfecting agents. In particular, the embodiment with the connector provided in the leak-tight partition 150 of the housing 144 of the driving system 140 is convenient—as it is shown in FIG. 3c. Additional protection with the cover (not shown in the drawing) enables protection of the connector from the contact with the used agents.

The driving system 140 is optionally sealed by means of the cover for the time of disinfection. Such sealing is not optional in the embodiment, in which the leak-tight partition 150 is not provided.

The coupling of the mechanical user interface 130 with the driving system 140 can be realized in different ways. The magnetic connection provides high leak-tightness by the partition 150, as well as using the driving system based on the electrically powered and controlled electronically engines for pulling the cable members. By using above-described coupling by the pistons working in the opening provided in the tight partition 150, it is possible to provide the experience of using the interface 130 the closest to the common endoscopes.

Figure 4:
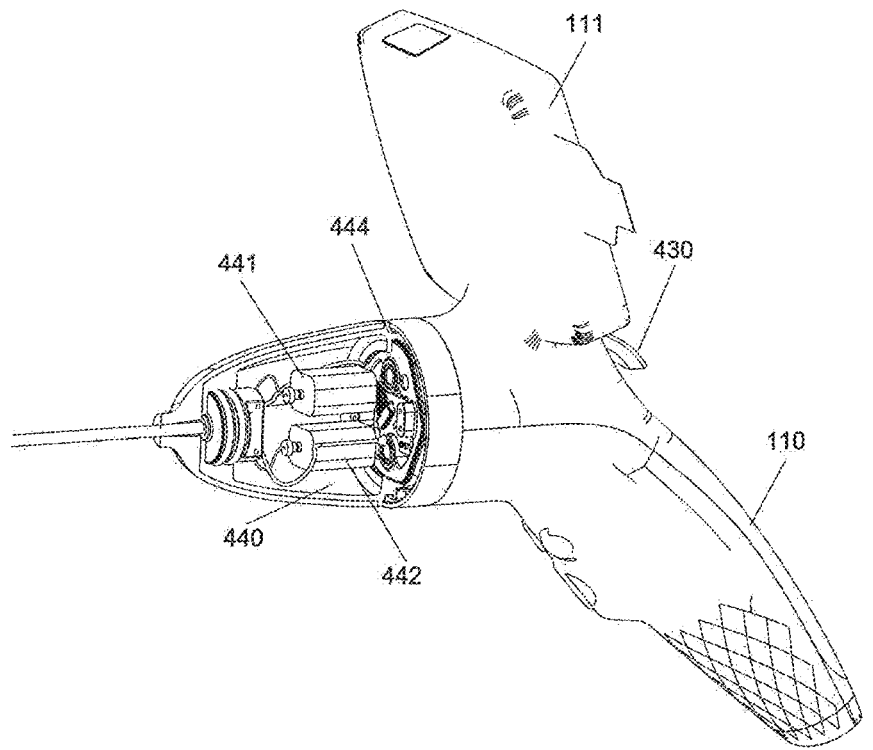
FIG. 4 presents an alternative embodiment in partial cross-section, in perspective.

Various constructions of the driving system are possible. In alternative embodiment shown in FIG. 4, the driving system 440 may comprise an electric engine with the wires closed in the sealed housing 444 or the electric engines controlled by means of the user interface 130. Such embodiment was shown in FIG. 4. The user interface 430 in this embodiment constitutes a lever with a system translating its movement to the electric signal fed to the driving system 440, but the joystick or the buttons may be used as well. Due to the fact that the electric coupling of the user interface with the engines 441, 442 located in the driving system 440 is used, it is possible to use an arbitrary interface in general. Such solutions facilitate the standardization and facilitate obtaining a modular construction of the device. It is also possible to use more complex interfaces with a greater number of buttons and/or leavers.

The advantages of the insertion device according to the invention include that it is possible to use many shafts with one handle, with various or identical functions. Such latter option enables better use of the handle 110 and carrying out the subsequent examinations with subsequent shafts 120, without waiting for finishing the process of preparation of the shaft for reuse. Analogue advantages are achieved during servicing and replacing the shafts, which are less expensive than the handle and more susceptible to damages.

The connection of the shaft with the driving system enabled providing the separable insertion device, in which elements located on the handle, vulnerable to conditions in which disinfection is carried out, and simultaneously not having the direct contact with the patient, can be detached for the time of disinfection and cleaned in less aggressive way and be less exposed to damages. Elongated shaft together with the drive and at least one cable enclosed inside are leak tight and can be disinfected separately. Additionally, it turned out, that by using the greater amount of replaceable shafts such solution enables using the handle in the continuous way while alternating preparation for reuse of two or more shafts. According to the invention, several possibilities to transmit signals actuating the driving systems were indicated and the image from the insertion device—mechanical, electronic and optoelectronic. Pneumatic and/or hydraulic solutions are also possible. The ergonomics of use was improved by giving the elements such shape so they will fit to each other only in one position.

The invention was described above in the context of embodiments of medical endoscopes provided with the cable members. Those embodiments as were foreseen only an illustration but not as limitation of the scope of protection, which is defined by the patent claims. In particular it is possible to use pneumatic, hydraulic or other driving systems, as well as other means for transmission of the force to the distal end of the endoscope, other than cable members.

The invention claimed is:

1. An insertion device comprising:
   a handle,
   an elongated shaft at least in part flexible, having a movable distal portion controllable with a user interface, and
   a driving system for transforming actuation from the user interface to a movement of the movable distal portion,
   at least one cable member extending along the elongated shaft from the movable distal portion to the driving system, said at least one cable member having a first end and a second end, the first end being connected to the movable distal portion of the elongated shaft and the second end being connected to the driving system,
   wherein the driving system is configured to convert the actuation from the user interface to a translatory motion of the at least one cable member, wherein the driving system has a housing closed with a leak-tight partition and leak-tightly connected to the elongated shaft on one side, and wherein the housing on the opposite side is provided with a first detachable leak-tight fastener, so that the driving system is detachable from the handle, wherein the handle is provided with a second detachable leak-tight fastener configured to be leak-tightly connected to the first detachable leak-tight fastener, wherein the driving system is configured to receive an actuation signal from the user interface via the leak-tight connection of the housing of the driving system with the handle when it is attached to the handle, and the at least one cable member is uninterrupted when the driving system is detached from the handle, wherein the driving system constitutes a pull-push gear with an eccentric intermediate element, having on one side two cable members reciprocally attached and on the opposite side the eccentric intermediate element is engaged reciprocally with a first piston and a second piston, wherein in the leak-tight partition two openings are provided, through which the first piston and the second piston protrude so that the first piston and the second piston are sealed in the two openings of the leak-tight partition by seals and they reciprocally affect the pull-push gear, whereas the user interface is a lever connected to a first pusher and a second pusher configured to push the first piston and the second piston, respectively.

2. An insertion device according to claim 1, wherein the movable distal portion is provided with an imaging device connected to a screen placed in the handle, by a connector of the housing provided in the housing of the driving system and a connector of the handle provided in the handle.

3. An insertion device according to claim 2, wherein the connector of the housing or the connector of the handle comprises touch-connectors.

4. An insertion device according to claim 1, wherein a light source is located in the housing of the driving system.

5. An insertion device according to claim 1, wherein the first detachable leak-tight fastener comprises a threaded connection with a gasket.

6. An insertion device according to claim 1, wherein the first detachable leak-tight fastener and the second detachable leak-tight fastener are complementary.

7. An insertion device according to claim 1, wherein the housing of the driving system is provided with a pneumatic connector.

8. An insertion device according to claim 1, wherein the housing of the driving system is provided with an optical connector.

*     *     *     *     *